United States Patent [19]
Durante

[11] Patent Number: 5,288,390
[45] Date of Patent: Feb. 22, 1994

[54] POLYCYCLIC AROMATIC RING CLEAVAGE (PARC) PROCESS

[75] Inventor: Vincent A. Durante, West Chester, Pa.

[73] Assignee: Sun Company, Inc. (R&M), Philadelphia, Pa.

[21] Appl. No.: 860,384

[22] Filed: Mar. 30, 1992

[51] Int. Cl.$^5$ .............................................. C10G 27/10
[52] U.S. Cl. .............................................. 208/3; 208/49; 208/262.5; 208/85; 210/263; 210/909; 585/319
[58] Field of Search ............... 585/319; 208/3, 49, 208/262.5; 210/263, 909

[56] References Cited
U.S. PATENT DOCUMENTS

| | | | |
|---|---|---|---|
| 3,671,421 | 6/1972 | Peck et al. | 208/49 |
| 3,928,484 | 12/1975 | Suggitt | 585/319 |
| 4,097,541 | 6/1978 | Sakai et al. | 585/319 |
| 4,234,749 | 11/1980 | Daly | 585/319 |
| 4,446,070 | 5/1984 | Huibers et al. | 502/170 |
| 4,814,545 | 3/1989 | Rule et al. | 210/763 |
| 5,156,748 | 10/1992 | Meunier et al. | 210/763 |

Primary Examiner—Helane Myers
Attorney, Agent, or Firm—Q. Todd Dickinson

[57] ABSTRACT

A process for the processing or upgrading of heavy oil fractions containing polynuclear aromatics is disclosed. The process comprises selectively oxidizing a feedstock under low severity conditions in a multi-phase system, wherein one phase is an aqueous and contains water-soluble catalyst, deoxygenating that product followed by hydroprocessing to yield a substantially mononuclear product.

27 Claims, 1 Drawing Sheet

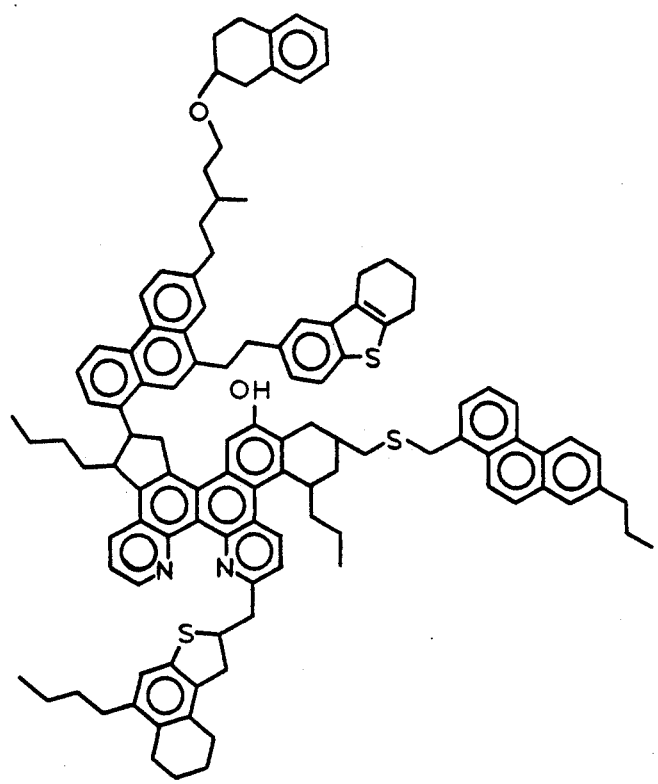
Fig. 1. (ASPHALTENE MODEL STRUCTURE)
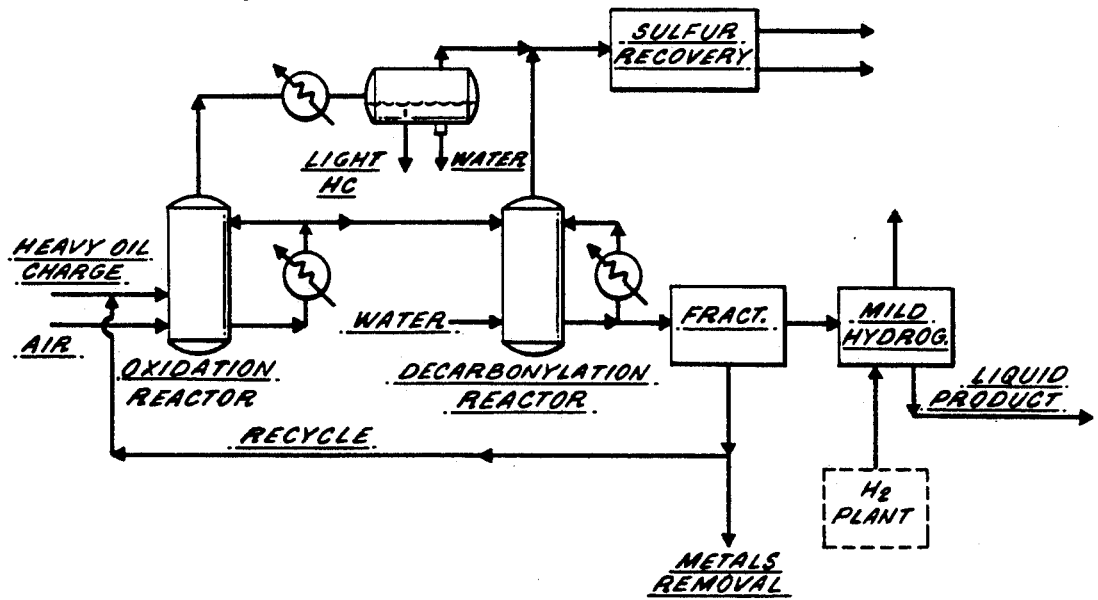
Fig. 2.

POLYCYCLIC AROMATIC RING CLEAVAGE (PARC) PROCESS

BACKGROUND OF THE INVENTION

A large portion of found oil and reserves can be characterized as heavy oil or bitumen, which is distinguished by a particularly high asphaltene or maltene fraction. These oils are often produced as emulsions with water when using secondary recovery techniques. Because heavy oils are ordinarily low cost feedstocks, there is often an economic incentive to convert these heavy oils (or other refractory hydrocarbons, such as coal derived liquids) into gasoline boiling range liquid fuels if processing costs can be kept low. This invention relates generally to an improved process for upgrading these heavy oils and bitumen into fuels or marketable syncrudes.

Considerable process technology already exists for upgrading heavy crudes, bitumens, and coal liquids, but most of the known processes are expensive and/or inefficient. Among those broad categories of primary heavy oil upgrading processes already known in the art are: carbon rejection or demetallation processes, hydrogen addition processes, and gasification or combustion processes.

Carbon rejection processes include delayed coking, Flexicoking, visbreaking, Fluidized Catalytic Cracking (FCC) (with the use of metals tolerant catalysts), Reduced Crude Cracking (RCC), and other versions of heavy oil cracking. A particular example of a carbon rejection process which may be used as a pre-treatment in advance of other upgrading steps is the Asphaltene Residual Treating (ART) process, which removes Conradson carbon fractions and metals components at otherwise low conversion.

An example of a gasification process is the gasification process developed by Texaco Development Corporation. This is a non-catalytic partial oxidation gasification process for generating principally hydrogen and carbon monoxide from mixtures of vacuum residue, SDA pitch, or other low hydrogen-to-carbon ratio feedstocks with water.

Hydrogen addition processes include: LC-fining, H-Oil, the Shell Resid Process, resid hydrocracking, resid hydrodesulfurization (HDS), and hydrodenitrogenation (HDN), most of which have been demonstrated on a commercial scale. Second generation hydrogen addition processes include: Microcat-RC, CAN-MET hydrovisbreaking, Veba Combi-cracking, and Dynacracking, all of which have been demonstrated primarily on a semi-commercial scale.

The advantages and disadvantages of these processes, as well as their general economics, are known in the art. For example, one significant disadvantage, particularly of carbon rejection processes, is the ordinarily high yield of coke or metals-containing solids which must be disposed of at considerable expense and some risk of environmental hazard. Additionally, gasification processes, such as the Texaco process, usually result in low liquid yields. Moreover, to achieve economically viable operation, these processes often require a scale which is much larger than the size needed to match the production rate of a particular heavy oil production site. Additionally, emulsified oils often must be demulsified prior to further processing.

Both hydrogen addition and carbon rejection processes, which often require the use of large quantities of solid catalysts, are also susceptible to reduced throughput and high catalyst replacement costs resulting from catalyst poisoning when processing heavy oils. This poisoning usually results from the deposition of either contaminant metals, high molecular weight refractory compounds (or coke derived therefrom), or sulfur or nitrogen containing heterocyclic compounds onto the catalyst surface. A review of this phenomenon is published in *Applied Catalysis*, (1985) 15, 197,225. Under certain circumstances these strongly-adsorbed poisons can react with catalyst components to form low melting eutectic compositions which can either sinter molecular sieves, zeolites, or other high surface area catalyst components or effectively block catalyst pores, in either case significantly reducing catalyst effectiveness. Additionally, beneficial acidic components can be partially neutralized and catalytic metallic components blocked by this virtually irreversible metals adsorption. Asphaltene and some resin fractions contain significant quantities of such poisons, which can be "cracked" onto the catalyst at high temperatures. Consequently, even though asphaltenes often comprise only 12% to 15% of typical heavy oil feedstocks, they disproportionally contribute to solid catalyst deactivation.

The following is a summary of the major problems encountered while upgrading heavy oils, bitumens, coal liquids, and other low hydrogen-to-carbon ratio feedstocks, by known refinery processes:

1. Severe reaction conditions are required.
2. Poor liquid yields with high gas and coke makes.
3. Formation of a poor quality coke which is not marketable.
4. High costs and materials-handling concerns associated with the use of hydrogen.
5. Deactivation of solid catalysts by contaminant metals, basic nitrogen compounds, and/or sulfur compounds. A separate processing step may be required to remove such compounds.
6. Required disposal of metals-laden solid catalysts, often as hazardous wastes.
7. Demulsification often being required prior to processing.
8. High viscosity feed produced requiring cutback with light solvents which must be sacrificed during subsequent processing.
9. Low volatility of heavy oils limits throughput in vapor phase processes.

Polynuclear Aromatics

A particularly significant concern in heavy oil processing are those compounds in the oils containing polynuclear aromatic backbones. These compounds constitute major components of the heavier oil fractions [M. M. Boduszynski, *Energy and Fuels*, (1988), 2, 597]. These components are relatively refractory, and the side-chains of the polynuclear aromatic molecules often condense during pyrolytic processing conducted above about 375° C., significantly increasing the coke or apparent Conradson carbon yield problem.

A traditional method of dealing with these polynuclear aromatics is to hydrogenate them, cleave the rings and convert the aromatics into generally more valuable molecules for fuels. However, those processes which use molecular dihydrogen as a process reactant, such as hydrocracking, hydrogenation, and hydrogen addition processes, incur the well-known problems associated with the use of molecular hydrogen, namely cost and materials handling difficulties associated with compressing and containing large quantities of gaseous hydrogen. When hydroprocessing polycyclic aromatic components to lower ring number or lower formula weight products, hydrogenation usually begins with a terminal ring and degrades rings successively inward, followed in each case by cracking of the then-saturated rings. If a center ring becomes hydrogenated, it usually undergoes dehydrogenation rather than cracking under mild hydroprocessing conditions. Thus, low yields of single ring (gasoline boiling range) aromatics are realized, high hydrogen consumption is required, and high yields of gas are produced. See U.S. Pat. No. 4,139,452, Beuther, et. al.; Wiser, et. al. *Ind. Eng. Chem. Prod. Res. Dev.* (1970) 9, 350 (1970); Penninger, et. al., ACS Symposium Ser. (1976) 32, 444; Langlois, et. al., *Adv. in Chem.* (1970) 97, 62; NIPER Cooperative Program Review Article, "Upgrading of Heavy Crudes: Probable Reactions of Problem Components During Hydrotreating" (1985).

If the center ring or rings of these polynuclear compounds, particularly the center rings of staggered-ring aromatics which are often found in asphaltenes, could be selectively hydrocracked or otherwise fractured, higher yields of single ring aromatics and concomitantly less hydrogen consumption would result. For example, in three ring aromatics such as phenanthrene, symmetrical cleavage of the center ring would result in two moles of gasoline-boiling range, single-ring aromatic molecules. However, no known commercial hydrocracking process exhibits this type of selectivity.

It would be also be advantageous to develop a process which uses only small quantities of catalyst, preferably as a finely divided solid slurry in a liquid phase, and/or one which operates below coking temperatures, at which rapid deposition of contaminant metals and the like occurs. It would be even more advantageous if the process employed a catalyst dissolved in a single liquid phases (i.e. homogeneous) or in one of mixed liquid phase, perhaps with the optional inclusion of a phase transfer catalyst. A process of this type would be expected to be less susceptible to poisoning by coking or metals deposition than existing processes which utilize large quantities of solid catalysts, since there would be essentially no surface onto which the deposition of contaminants and coke could occur. The present invention provides such a solution.

The Polycyclic Aromatic Ring Cleavage (PARC) Process described herein ameliorates many of the problems identified with heavy oil or residuum upgrading which are well-known in the prior art described above. In particular, it results in the selective fracturing of large multi-ring aromatics without incurring much of the expense associated with high conversion hydroprocessing. It also minimizes the yield losses associated with traditional carbon rejection processes and the poisoning problems associated with the use of resid or heavy oils in processes requiring a large volume of solid catalysts.

Further advantages of the PARC Process can be summarized as follows:
1. Increased liquid yields of high-octane gasoline blending (aromatic) components.
2. Decreased hydrogen consumption.
3. Low yield of light gas cracking products.
4. Partial desulfurization of feed.
5. Mild operating conditions.
6. Avoidance of large quantities of metal laden solid catalysts requiring disposal as hazardous waste.
7. Long catalyst life in the presence of contaminant metals often found in residua.
8. Ability to use emulsified oils directly in process without pre-demulsification step.

The process of this invention generally comprises the selective partial oxidation of the polycyclic aromatic ring components of heavy oils in liquid phase, in particular the center ring of three-member ring systems, followed by deoxygenation (decarbonylation or decarboxylation) of the first step product and finally mild hydrotreatment, resulting in high yields of single ring aromatic fuels or marketable syncrudes. This is accomplished at mild oxidation conditions under which both coking and non-selective autoxidation are minimized. Deposition of contaminant metals by cracking onto a solid catalyst is also avoided.

Variations on the process include the combination of the oxidation and decarbonylation steps into a single process step, and the conducting of the oxidation step in situ in an underground oil reservoir. A related process is the utilization of the first step oxidation process to prepare substituted phenanthrenequinones from the corresponding substituted phenanthrenes.

RELATED REFERENCES

The following are related references to the invention contained herein:
1. U.K. Patent GB2 132 107 A, Feb. 3, 1982, Huibers, et al., assigned to Hydrocarbon Research, Inc. (HRI).
2. U.K. Patent GB 2094 827 A, Feb. 3, 1982, Huibers, et al., assigned to Hydrocarbon Research, Inc. (HRI).
3. U.S. Pat. No. 4,446,070, May 1, 1984, Huibers, et al., assigned to Hydrocarbon Research, Inc. (HRI).
4. U.S. Pat. Nos. 4,496,778 and 4,496,779, Jan. 29, 1985, Myers, et al., both assigned to Exxon Research & Engineering Co.

The present process is distinguishable from the HRI oxycracking process disclosed in references 1-3 in that PARC is a more selective process for cleavage of central aromatic rings without side chain oxidation or cleavage, and does not require the pre-dealkylation step which is required in all three references. This is due primarily to the excess side chain oxidation which occurs in the HRI process, and which is minimized in the present invention. Also, the present process is ordinarily a slurry or liquid phase or mixed liquid phase process, whereas Oxycracking (the process of the HRI references) is conducted in the vapor phase. PARC Process reaction conditions are also much more mild than those of Oxycracking and result in significantly less coke and metals-contaminated solid catalyst residue. In the PARC Process, moreover, the reaction can also optionally proceed through either ketone or carboxylic acid intermediates which are deoxygenated in a separate second step. The HRI process, conversely, is a one-step oxidation process.

The Exxon patents, reference 4, primarily teach the use of a water-soluble osmium/copper catalyst for the selective oxidation of olefins. They do not address the use of osmium/copper catalysts for the oxidation of aromatics and do not contemplate nor suggest the catalyst's potential ability to upgrade whole oils or heavy oil or resid fractions. The present invention for the first time employs this catalyst and/or others to oxidize both pure aromatics and whole oil fractions containing some aromatics.

In addition to the Exxon patents and papers, the stoichiometric reactions of $OsO_3(NR)$ type compounds with alkenes has been described by W. P. Griffith et. al., *JSC, Dalton Trans.* (1986), 1035 and references therein. The ruthenium tetroxide catalyzed oxidation of coals has been described by L. M. Stock and S. H. Wang, *Fuel* (1986) 65, 1552. However, this reference describes the use of oxidants other than molecular oxygen, and is clearly differentiable from the present invention. The PARC process can also be easily distinguished from processes for the non-catalytic oxidation of petroleum tars and bitumen which are known in the art. These processes are generally not selective to appropriate intermediates for the PARC process.

For example, in one process described in the literature, which is conducted at 250° C., ~7 atm, pH=2-3 and 1:10 ratio of tar:benzene for up to 6 hours contact time, asphaltenic components increased in a straight-run distillation residuum after air oxidation due to incorporation of about 41% total oxygen. The product distribution was unselective, yielding 35-45% esters, 25-30% hydroxyls, 20-30% carboxyls, and only 5-10% carbonyl oxygen. See: V. I Antonishin & V. I. Gaivanovich (Lvov Polytech. Inst.) *Neflekhimiya* 27 #5:686-91 (Sep.-Oct., 1987). These results are in contrast to the selectivity envisioned for the oxidation step of the PARC process. Furthermore, no deoxygenation was described nor contemplated in the Russian reference.

In another report, C. R. Phillips & I. C. Hsieh, *Fuel* (1985) 64, 985, which describes the non-catalytic air oxidation kinetics of Athabasca bitumen, the fraction of oxygen converted to CO, $CO_2$ rose from about 9% at 200° C. to about 57% at 300° C. Hence, non-catalytic oxidation processes can be shown to be much less selective than the PARC process to liquid products, especially at temperatures above about 200° C.

SUMMARY OF THE INVENTION

In the present invention, a low severity process is disclosed for the upgrading of hydrocarbonaceous feedstocks containing polynuclear aromatic compounds, particularly feedstocks containing significant fractions of heavy oil. Broadly, the process comprises the steps of: (1) selectively oxidizing the feedstock under mild oxidation conditions in a multi-phase system, including at least one aqueous phase, employing a water-soluble oxidation catalyst specifically chosen to catalyze the selective oxidation of non-terminal aromatic rings of polynuclear aromatic compounds in the feedstock; (2) deoxygenating the product of the oxidation; and (3) hydroprocessing the product of the deoxygenation to yield substantially mononuclear products. It is also contemplated that the effluent of step (1) can be separated into generally aqueous and non-aqueous phases, and that the aqueous phase containing the water-soluble catalyst may be recycled to the selective oxidation step.

BRIEF DESCRIPTION OF THE DRAWINGS

FIG. 1 describes a structure of a model asphaltene molecule.

FIG. 2 describes a schematic process flow diagram for an embodiment of the present invention.

DETAILED DESCRIPTION OF THE INVENTION

Asphaltene Structure

One of the primary components of heavy oils is the asphaltenes. They are also among the most notoriously difficult to upgrade. If a new process is going to significantly address the problem of upgrading heavy oils, it had best focus on how to attack these asphaltenes.

Recent analytical separation, spectroscopic, and reactivity characterizations of asphaltenes have now been conducted which suggest a revised, more open structure for the average asphaltene "molecule" than had previously been recognized. One conception of this average structure is shown in FIG. 1.

This more recent concept differs from older views in that large (i.e. greater than 10 ring) pseudo-aromatic "sheets" as previously proposed probably do not exist in most virgin oils (although they may exist in coals). Additionally, there is probably not a high incidence of large core nuclei containing more than six aromatic rings; a staggered ring configuration of three or more adjacent rings is favored.

About half the sulfur present in these compositions is probably in easily broken thioether linkages, and amphoteric functionalities are present in the larger ring systems. Chelating coordination sites for metals such as V or Ni are also present.

Ordinarily, one is unlikely to distill asphaltenes without pyrolyzing them to higher polymers or coke and generating significant amounts of cracked products from side chain cleavage in the process. This suggests that virgin oils probably contain asphaltenic fractions of generally lower formula weight than those of heat-treated or distilled oils. This further suggests that the chemistry identified with certain model compounds, for example methylphenanthrene, could likely be comparable to the chemistry of unpyrolized asphaltene molecules. Therefore, a preferred means for illustrating how the present invention attacks the problem of asphaltene processing is by using a model molecule which illustrates the phenanthrene-type linkages found in asphaltenes. The simplest of these model compounds is methylphenanthrene. The process of the present invention and its chemistry are therefore best understood conceptually using methylphenanthrene as an exemplar, which represents a fragment of a generic asphaltene molecule.

Process of the Present Invention

I. Oxidation Step

In the first step of a preferred embodiment of the present process, the designated feedstock is partially or selectively oxidized to one or more intermediate oxygenates. The oxygenation is preferably carried out under mild oxygenation conditions, thereby avoiding many of the pyrolysis and other problems associated with prior art processes. These mild oxygenation conditions may vary, but preferably constitute a temperature of less than 250° C., more preferably between approximately 100° C. to 180° C., and most preferably between approximately 120° C. to 180° C.; a pressure of approximately 0 to 2000 psig, more preferably between approximately 100 to 2000 psig and most preferably between approximately 300 to 500 psig; and at least one oxidant which contains molecular oxygen. A diluent may be optionally added to the oxygen. The process is also preferably conducted in the absence of molecular hydrogen.

The selective oxidation step is carried out in a multi-phase system which includes at least one aqueous phase, in a batch, semi-batch, or continuous reactor. A stirred tank reactor is preferred. The aqueous phase includes a water-soluble oxidation catalyst which will be described in greater detail below. Besides facilitating the oxidation/catalysis process, the presence of water helps suppress coking processes and dissolves soluble catalysts. The catalyst is specifically chosen to catalyze the selective oxygenation of the non-terminal rings of the polynuclear aromatic compounds found in the feedstock, such as the methylphenanthrene discussed above. In an alternative embodiment, the catalyst may be a solid catalyst slurried in the aqueous or mixed phase. Additional liquid phases may also be present, which ordinarily constitute hydrocarbons or other organic compounds.

The components of the oxidation step must be well-mixed to ensure high contact area between the immiscible liquid phases. Surfactants may optionally be added to promote the dispersion of these immiscible phases. Without being limited by a particular reaction mechanism, using a methylphenanthrene molecule as a model, some possible intermediates formed in this oxygenation are illustrated as follows:

As shown, the oxidation step is primarily directed to the selective oxygenation of the non-terminal aromatic rings of polynuclear aromatic compounds found in asphaltenes, more preferably the center ring of three-ring systems. It is also preferably selective for the oxidation of polynuclear aromatic compounds over the non-aromatic functionalities of those compounds, especially alkyl or other side chains, which may be present.

The selective oxidation step results in the formation of intermediate oxygenates which are preferably alcohols, ketones, quinones, carboxylic acids, etc. They all result from oxygenation of the central aromatic ring. Side chain oxidation, (4), or terminal ring oxidation, (5), are undesired and contribute to poor selectivity along with over-oxidation to burn products, (6). Trione formation is also generally undesired due to the difficulty in deoxygenating such a molecule in subsequent processing steps, but is not excluded as a possible reaction path.

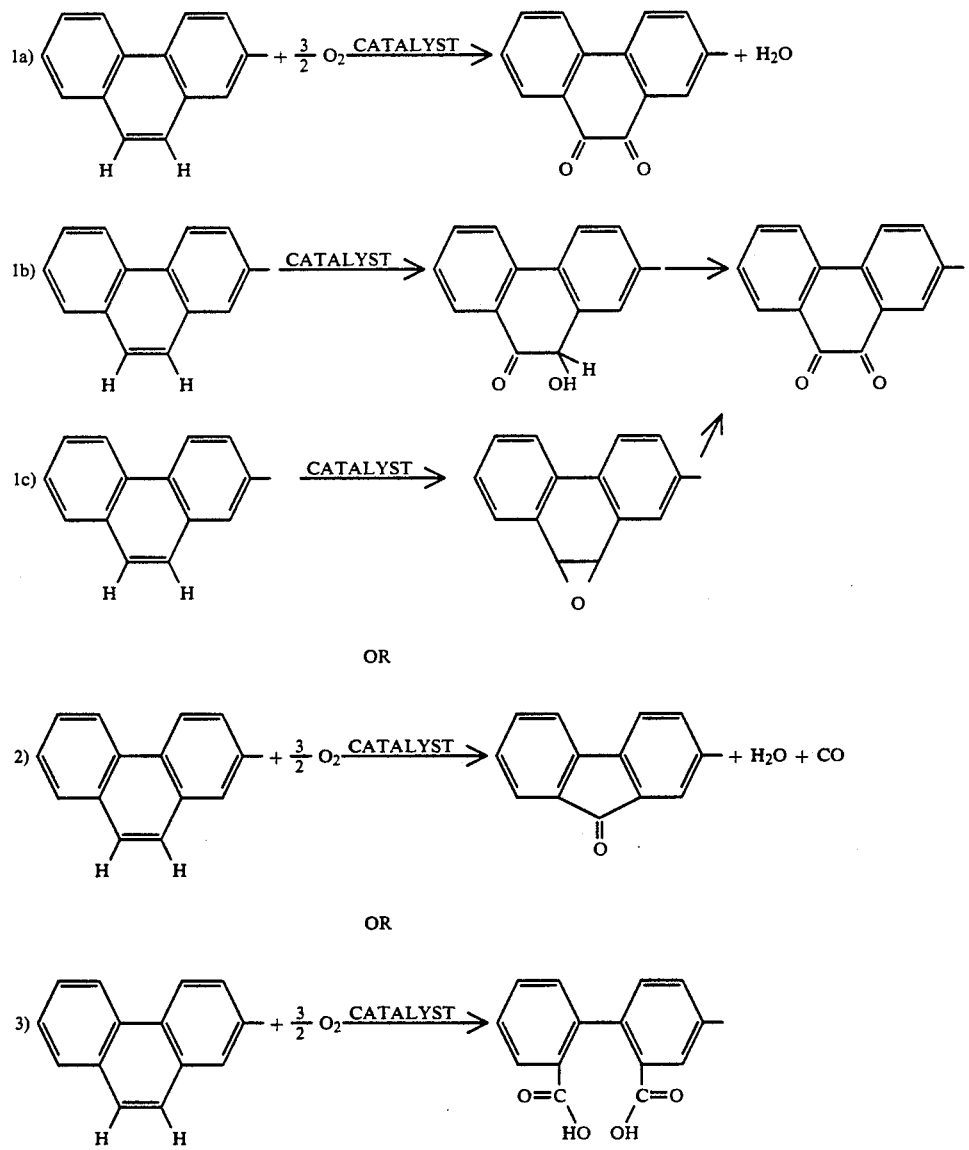

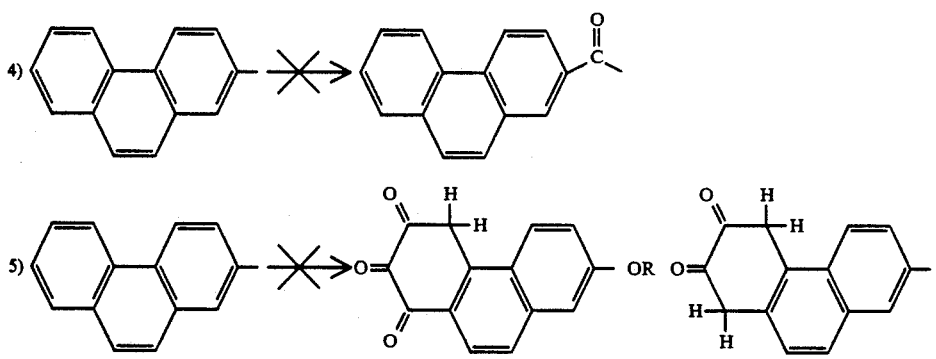

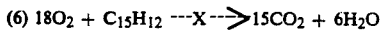

(6) $18O_2 + C_{15}H_{12} \xrightarrow{X} 15CO_2 + 6H_2O$

If reaction (4) were to significantly contribute to oxygen consumption, dealkylation would then probably be required as a first process step in order to avoid formation of carboxylic acids without rupturing the center ring. Thus, this is an undesired reaction.

In an alternative embodiment, the aqueous phase containing the water-soluble oxidation catalyst may be separated from any non-aqueous phases following the oxidation step, and the catalyst-containing aqueous phase or its concentrate recycled to the process vessel for the selective oxidation step.

Additionally, a portion of the heavy fraction may be withdrawn from a batch reactor to remove concentrated metals fractions and the aqueous phase returned to the reactor. These metal values could be recovered by separate conventionally-known processing steps, if economically justified.

Since there is often sulfur present in heavy oil feeds and C—S bonds are relatively weak, it is expected that the oxidation step could possibly generate significant amounts of $SO_2$, depending on reaction conditions. Catalytic or non-catalytic oxidative demetallation could also occur in this step depending on process conditions and the type of feedstock. Conditions favoring oxidative demetallation would probably be high temperatures (>200° C.) and high oxygen partial pressure. The occurrence of these reactions might result in an additional advantage for the process if subsequent hydroprocessing or other steps would otherwise be required to remove metals or sulfur-containing fractions.

Catalyst

Several catalysts have been found useful in promoting the selective oxidation step. As discussed above, these are preferably either water soluble or capable of being slurried in the aqueous phase. They also preferably comprise complexes containing a transition metal or metals, more preferably a Group VIII metal or metals. It is also preferred that the catalyst contains ligand structures which incorporate functionalities which are themselves difficult to oxidize, such as, for example, C—F terminal bonds instead of C—H bonds.

A specific catalyst which has been found to be useful is the $OsO_4/Cu$/pyridine catalyst described in U.S. Pat. Nos. 4,496,778 and 4,496,779 (which are incorporated herein by reference). Other useful catalysts or catalyst precursors include compounds of ruthenium, iron, nickel, or palladium which contain chelating ligands with electron withdrawing functionalities, and which are capable of forming high oxidation state oxometal complexes under reaction conditions. Such catalysts include, but are not limited to, [Ru(dichlorobipyridine)$_2$($H_2O$)(py-X)]$^{+2}$ (where X is Cl, $CF_3$, or $COCH_3$, or other electron withdrawing substituent), alone or in combination with co-catalysts such as $Cu^{+2}$ or HPA-8, a vanadium-containing polyoxometallate. Trinuclear ruthenium carboxylate complexes such as $Ru_3(O_2CR)_6L_3{}^n$, (where R=$CH_3$, $C_2H_5$, $C_2F_5$, etc.; L=$H_2O$; n=0,+1), are also useful, alone or in combination with copper(I) salts as co-catalysts. In the preferred embodiment, oxidation catalysts are generally added as aqueous solution of millimolar concentrations, but catalyst concentrations may be adjusted over a wide range of reasonable reactor contact times to achieve high conversions.

Other co-catalysts may also be effectively utilized in the oxidation step, especially for the reoxidation of the transition metal complex catalysts. These co-catalysts are also preferably water-soluble, although they may alternatively be slurried. The preferred co-catalysts contain metal ions selected from the group consisting of vanadium, copper, iron and cobalt, although additional transition metal-containing co-catalysts may be also be useful.

Feedstocks

The present invention may be effectively used to upgrade any hydrocarbonaceous feedstock having asphaltene or substituted phenanthrene-containing components. Preferred feedstocks include crude petroleum, atmospheric residuum, vacuum residuum, heavy oil, asphalt, and coal liquid or other products of a coal liquefaction process. The feedstock is normally introduced into the oxidation step alone, although it may alternatively be introduced as an oil/water emulsion. The feed may also optionally be dissolved in a lighter hydrocarbon or other solvent, such as kerosene or toluene, prior to introduction. This is often useful for heavier residuum feeds. It is also contemplated within the scope of the invention that the feedstock can be processed in batch, semi-batch, or continuous operations.

II. Deoxygenation Step

Following the selective oxidation step, the intermediate oil fractions, the newly-formed center ring oxygenates, are then deoxygenated to preferably yield phenyl compounds, most preferably substituted biphenyls. It is these compounds which, in the third step, are hydroprocessed or hydrotreated to form mononuclear aromatic products, i.e. benzene derivatives. After separation of the non-water soluble organic fractions using any known technique, these are passed to a second reactor containing aqueous base and optionally a decarbonylation catalyst.

The deoxygenation step is preferably carried out in an strongly alkaline environment, more preferably an alkaline environment comprising approximately two moles of base per each liter of liquid water. Useful temperature ranges for this step are between approximately 25° to 375° C., preferably 50°-200° C., most preferably 110°-160° C. Reactor pressure is kept high enough to maintain at least some liquid water in the reactor. The preferred contact time is between approximately 0.5 hours to 4 days.

It is contemplated that the second step deoxygenation may be accomplished by either decarbonylation or decarboxylation. Reactions illustrating the deoxygenation step according to the present invention are shown as follows:

phase is required. Intermediate quinones could also be further oxidized in a second stage oxidation reactor to carboxylic acids which could then be decarboxylated either in situ or in yet another oxidation stage (see equation 8) by oxidative decarboxylation. Oxygen must be introduced to accomplish oxidative decarboxylation.

The deoxygenation process is preferably carried out using a catalyst specifically chosen to catalyze the deoxygenation. The preferred deoxygenation catalyst contains Group VIII metal or metals, preferably ruthenium or rhodium. The ruthenium is preferably in the +2 oxidation state and the rhodium in the +1 oxidation state. Examples of preferred deoxygenation catalysts include: soluble ruthenium (II) complexes of macrocyclic ligands containing at least one triphenylphosphine ligand.

It is also contemplated that soluble metal complexes which can catalyze the water gas shift reaction under basic conditions may also be useful for catalyzing the decarbonylation of dione intermediates which form in the oxidation step.

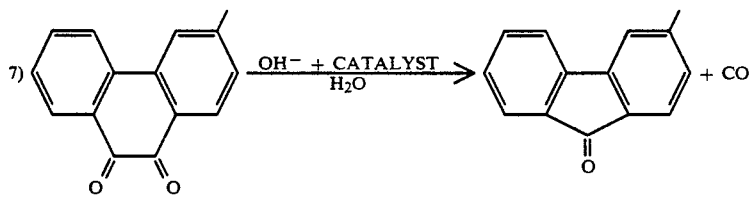

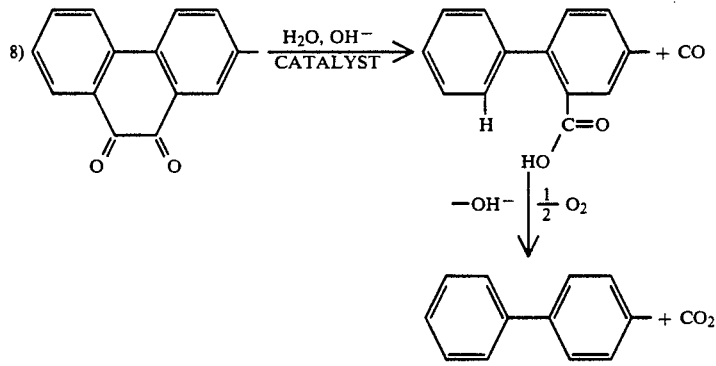

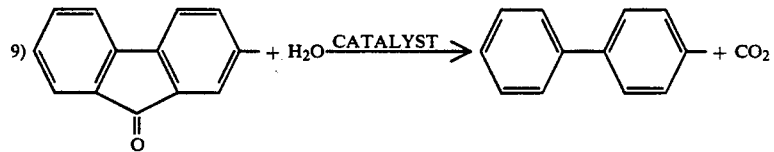

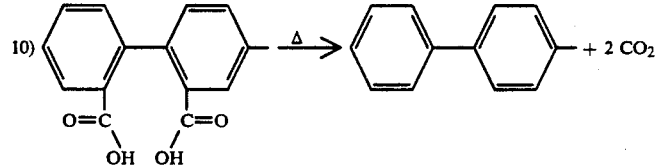

Because of the build up of carbonates in the aqueous phase or as precipitated solids, once the reactor is cooled, periodic replacement of the alkaline aqueous As an alternative embodiment, it is contemplated that the first and second steps (i.e. oxidation and deoxygenation) may be combined into a single process step with the addition of aqueous base to the first step oxidation reactor solutions and, optionally, a decarbonylation catalyst in combination with the preferred Os/Cu catalyst described above.

III. Hydroprocessing or Hydrotreating Step

The present process is completed by a third step which converts the phenyl compounds formed in the deoxygenation step into single ring aromatics. An example of the reaction stoichiometry is as follows:

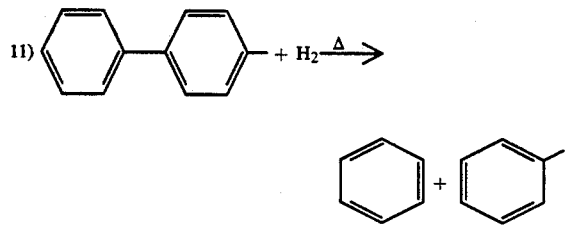

In a preferred embodiment, the hydroprocessing step comprises charging the product of the deoxygenation step and hydrogen into a reaction zone at a temperature above about 535° C., a pressure in excess of about 100 psig, for a residence time of about 5 to 50 seconds, and at a hydrogen to hydrocarbon equivalent mole ratio between about 2:1 to 30:1 at the reactor inlet. The hydrocarbon moles are calculated assuming that the entire organic fraction is biphenyl. The desired reaction products are then separated from unconverted material and hydrogen by any conventional means. In a more preferred embodiment, the temperature range in the hydroprocessing reaction zone is between about 650° to 760° C., the pressure range is between 300 to 800 psig, the residence time is between about lo to 30 seconds, and the hydrogen to hydrocarbon equivalent mole ratio is between about 5:1 and 20:1.

The hydroprocessing step is ordinarily conducted in the absence of catalyst under mild conditions, an example of which is shown in U.S. Pat. No. 3,210,432, Richter, incorporated herein by reference. Thus, two moles of single ring aromatics are produced per mole of 3-ring aromatic starting material rather than the one mole expected from hydrocracking. This translates to increased liquid yields compared to hydrocracking of whole heavy oil fractions.

Overall Process Conditions

Thermodynamic calculations on model reactions demonstrate that all the anticipated steps are exoergic. Decarbonylation is more favorable at lower temperatures, however. The exothermicity of the oxidation process can be utilized in part to heat the water for the second step, in integrated processing schemes such as with steam drive secondary recovery on sight near an oil production site, or to cogenerate electricity. Operating temperatures for the oxidative process step will be determined not only by catalytic reaction requirements but also by the requirements of efficient steam utilization. Subcritical operation is desired, and the upper temperature limit for the first two steps is set by the critical temperature of water. This latter consideration will contribute to overall favorable process economics.

Process Flow Diagram

A preferred embodiment of the process of this invention is illustrated schematically in the flow diagram of FIG. 2.

EXAMPLES

Example 1

Catalytic oxidation of phenanthrene to phenanthrenequinone was conducted as a model for an aromatic fraction of a heavy oil as follows:

Phenanthrene (22.4 millimoles) was dissolved into a solvent consisting of 80 volume percent tetramethylenesulfone (sulfolane) and 20 volume percent water. Cuprous bromide (1.04 millimoles) and a solution of osmium tetroxide in t-butyl alcohol (0.049 millimoles Os) were added to the solution of phenanthrene along with 3.31 millimoles of pyridine. The mixture, which contained some insoluble material at this point, was sealed into a glass-lined 50 cc autoclave stirred tank reactor fitted with a magnetically coupled stirring impeller, gas inlet tubes, a fore pressure regulator and microflow device leading from a thermostatted oxygen reservoir, and an external heater. After flushing with pure oxygen several times, the reactor was heated to 180° C. with vigorous stirring and the pressure adjusted to a total of 400 psig by addition of a quantity of oxygen once the reactor was temperature equilibrated. As oxygen was consumed by the reaction in the liquid phase, the fore pressure regulator admitted more oxygen to maintain the pressure in the reactor at 400 psig during the course of the run. The rate of consumption and the total consumption of oxygen were precisely measured with elapsed time over a 6 hour period. The reactor was then cooled under oxygen in an ice bath and sampled by complete dissolution of the liquid and solid phases into various solvents. Gas chromatographic/mass spectral analysis was used to establish the product distribution. Results from the experiment were a 77 weight percent conversion of phenanthrene with an 89% molar selectivity to phenanthrenequinone. The average turnover rate per hour based on gas uptake measurements was 129 moles per mole Os per hour.

Example 2

The experiment of Example 1 was repeated but at 120° C. with a slightly lower stirring rate. Analysis of the products gave 18.8 weight percent conversion and 93.9 molar percent selectivity at an average turnover rate of 29.5 mol/mol hr.

Example 3

Phenanthrene (33.7 millimoles) was dissolved with cuprous bromide (1.46 millimoles of Cu), potassium osmiamate (0.3433 millimoles), and pyridine (4.74 millimoles) into 80 vol. % sulfolane/20 volume percent water (30 ml solvent) and placed into a borosilicate glass Fisher-Porter pressure tube along with a pancake Teflon coated magnetic stirring bar. The tube was fitted with a thermocouple and a gas inlet system and connected to an oxygen reservoir. After flushing several times with pure oxygen, the tube was heated with stirring to 120°-126° C. for 6.2 hours. Oxygen pressure over the stirred reactor was manually adjusted every 10 minutes to 100 psig and the reservoir pressure and reactor pressure before each addition noted to determine the amount of oxygen consumed with each addition. Gas chromatographic/mass spectral analysis of products as in Example 1 indicated 33.5 weight percent conversion and 99.6 molar percent selectivity to phenanthrenequinone.

Example 4

A blank run was performed as follows: The experiment of Example 1 was repeated without addition of osmium, copper, or pyridine at 180° C. The conversion was found to 1 weight percent with a 17.5% selectivity to phenanthrenequinone at the end of the run.

Example 5

An experiment in the equipment described in Example 3 was used to examine the oxidation of 2-ethylanthracene (24.4 millimoles) using 0.071 millimoles of $OsO_4$ in t-butanol, 3.0 millimoles of Cu(1), 4.79 millimoles of pyridine in 30 ml. of 80% sulfolane/water solvent at 120° C. for 5.5 hours. Analysis of the products indicated 81 weight percent conversion with 96.5% selectivity to ethylanthraquinone. This demonstrated the selective nature of the oxidation for central aromatic rings rather than alkyl side chains.

Example 6

An experiment was conducted in the apparatus described in Example 3 using 2-methylphenanthrene as substrate (2.59 millimoles), 0.14 millimoles of potassium osmiamate, 1.46 millimoles of cuprous bromide, 3.79 millimoles of pyridine in 30 ml of 80% sulfolane/water at 120° C. for 6.25 hours. Major products were the dione of the central ring and the dione of the terminal ring. No side chain attack was noted. In a similar experiment using the apparatus of example 1 and $OsO_4$ catalyst at 180° C., an average turnover rate of 161 mol/(mol hr) was noted.

Example 7

The apparatus of Example 1 was used, into which was introduced 0.061 millimoles of $OsO_4$, 1.3 millimoles copper, 4.05 millimoles pyridine, and 27.75 millimoles of 1,10-phenanthroline substrate at 400 psig $O_2$ overpressure (including vapor pressure of solvent). The run was conducted at an internal temperature of 120° C. for 6 hours. The average turnover rate of oxygen consumption was 53.3 mol/(mol/hr), and the only oxidation product of the substrate found in high concentration was the 5,6 quinone. No N-Oxides were found.

Example 8

The apparatus of example 3 was used to study the oxidation of dibenzothiophene at 120° C. for 4 hours as a model for sulfur-containing residual oils. $OsO_4$ (0.095 millimole) was used as the catalyst along with 2.93 millimole copper(I), and 4.74 millimole pyridine promoter, in 30 ml of 80 vol. % sulfolane/water solvent. Only 3.3% conversion was noted to at least 4 products.

Example 9

The apparatus of Example 1 was used to study the oxidation of dibenzothiophene under essentially the same conditions as shown in Example 1 at 180° C. Gas chromatograph analysis of the reaction product in the liquid phase indicated 9.4 wt. percent conversion to only one major product (98.1 area percent selectivity) which was not identified.

Example 10

The apparatus of Example 3 was used to study the catalytic oxidation of anthracene at 120° C. using essentially the same conditions described in Example 3 but for 6 hours. Conversion was found to be 87.1 wt. percent and selectivity 96% to the 9,10-quinone.

Example 11

The all-glass apparatus of Example 3 was used to study the oxidation of toluene at 120° C. using 3.1 grams of toluene and 0.343 millimole of potassium osmiamate, along with copper and pyridine as described above in Example 3. Virtually no conversion of toluene was noted. This result lead us to believe that light solvents such as non-polynucleararomatic kerosene or lighter fractions or toluene itself could be used as diluents for heavy oils undergoing step 1 oxidation.

Example 12

Preparation of Asphaltenes

Asphaltenes used in the following Examples were prepared from oil derived from the Anderson-Goodwin lease of the Midway Sunset field near Oxnard, Calif. Two hundred grams of oil were mixed with an equivalent volume of toluene and heated with stirring until homogeneous, approximately 15 minutes. After cooling to room temperature, the solution was filtered and 1.2 g of solid material removed and discarded. The toluene solution was then slowly added to a ten-fold volumetric excess of hexane at room temperature with vigorous stirring, and the resulting mixture allowed to stand for 1 hour. After filtration to remove the first crop of precipitated asphaltenes, the filtrate was allowed to stand (covered) overnight. A second crop of asphaltenes was recovered the next morning, combined with the first crop, and washed several times by reslurrying in hexane. After filtration, the resulting solids were dried in a vacuum at 50° C. for 1 hour. 8.3 g (4.2%) of dried solids were recovered.

Example 13

The apparatus and procedure of Example 1 was used to study the catalytic oxidation of an asphaltene fraction (4 grams) prepared according to Example 12 using 0.04 millimoles $OsO_4$ 1.04 millimoles cuprous bromide 3.31 millimoles pyridine, using a 50 vol percent toluene/water mixture as a liquid phase at 180° C., 400 psig overpressure of oxygen plus solvent vapor pressure, for 6 hours. 16.2 total millimoles of oxygen were absorbed for an average turnover rate 55.0 mol $O_2$ per mol Os per hour.

Example 14

The experiment of Example 13 was repeated using 5 grams asphaltene, 0.061 millimole Os, 1.3 millimole copper, and 4.17 millimole pyridine in 80 vol. percent sulfolane/water solvent. Oxygen taken up was 12.2 millimoles. Infrared analysis of a dried organic fraction of the product indicated the likely presence of ketones in the oxidate.

Example 15

The apparatus and procedure of Example 3 was used to study the oxidation of 10 grams of a clarified slurry oil in 30 ml of 80% sulfolane/water mixture along with 0.071 millimole $OsO_4$ (in t-butanol), 2.93 millimole cuprous bromide, and no pyridine at 115° C. for 5.25 hours. Oxygen was taken up (68 millimoles).

Example 16

The apparatus and procedure of Example 3 was used to study the oxidation of an 8 gram sample of a powdered bituminous coal (22% volatility) from western Virginia, U.S.A. using 0.343 millimole of potassium osmiamate as a catalyst precursor, 2.93 millimole of cuprous bromide co-catalyst, and 4.74 millimole pyridine in a liquid phase consisting of 30 mi of 80 vol. % sulfolane/water at approximately 120° C. for 6.5 hours. Oxygen was taken up (ca. 58 millimole).

Example 17

A blank run was conducted as per Example 3, but without the addition of Os or pyridine. 1.2% conversion was noted, but no dione was formed. The majority of the products were brominated from the co-catalyst.

Example 18

A blank run was conducted as per Example 17, but without substrate. Virtually no conversion products were detected.

Example 19

A run was conducted as per Example 3, but replacing cuprous bromide with cupric chloride. Lower conversion and selectivity than found in Example 3 were noted.

Example 20

A semi-batch reactor with flowing oxygen (8% mixture at STP) was used to oxidize a virgin water/oil emulsion which had been obtained from a commercial heavy-oil secondary recovery operation in California, USA. Temperature during the run was ca. 200° C. at 1450–1490 psig total pressure using $KOsO_3N$, cuprous bromide and the pyridine catalyst system added to a small amount of additional water. Infrared and simulated distillation analyses were conducted on a recovered, dried, and diluted oil fraction which indicated the presence of ketones and materials with retention times identical to phenanthrenequinone (in a pyrolytic GC experiment).

Example 21

The oxidate of Example 20 was partly dewatered and mixed with 20 ml. of 2M KOH (aq.) and 1 gram of solid cupric oxide in a Teflon-lined stirred tank reactor equipped with a magnetically-coupled high speed impeller. After flushing with argon, the reactor was sealed and the mixture was stirred at high speed for 5 hours at 190°–210° C. at autogenous pressure. After cooling to ca. 40° C., gas chromatographic analysis of the head space gases indicated the presence of CO, $CO_2$, and $SO_2$. Demulsification was accomplished by slowly stirring in about 6 cc of toluene to the filtered product (to remove CuO etc.), centrifuging at 9000 RPM for several minutes, and followed by settling overnight. About 20 cc of additional toluene were added to the isolated organic fraction and the mixture was heated for 15 minutes on a hot plate. After cooling to room temperature, the solution was added to about 40 cc of hexane with vigorous stirring and allowed to stand overnight. The precipitated asphalt fraction was isolated by filtration, washed with hexane, and dried in a vacuum oven at 50° C. for one hour. The dried solids recovered were 3.2% of the original weight of the oxidate mixture used. A control experiment with an oxidate emulsion which had been sealed in a stirred autoclave along with additional water under argon and heated with vigorous stirring to about 200° C. for 2 hours then cooled and separated as above resulted in an asphaltene fraction representing 8.4% of the weight of the original emulsion.

Example 22

Using the model compound phenanthrenequinone, we have been able to deoxygenate and to reduce carbon number under mild fluid solution conditions. Aqueous base in contact with the quinone at 200° C. (in solvent) was effective for conversion of the quinone to fluorenone (major product) along with lesser amounts of biphenyl and the 2-aldehyde derivative of biphenyl. $CO_2$ and $H_2$, possibly resulting from the water gas shift reaction of the CO primary product, were also detected.

20 cc of the partly dewatered oxidate reaction product from the above example was mixed with 20 cc of 2M KOH (aq.) and 1 g of solid CuO in a Teflon-lined stirred tank reactor equipped with a magnetically-coupled high speed impeller. After flushing with argon, the reactor was sealed and the mixture was stirred as around 2000 rpm for 5 hours at 190°–210° C. at autogenous pressure, and then cooled to about 40° C. GC analysis of the head space gases indicated the presence of CO, $CO_2$, and $SO_2$. Demulsification was accomplished by slowly stirring in about 6 cc of toluene to the filtered product (for the removal of CuO), centrifuging at about 9000 rpm for several minutes, and settling overnight.

Example 23

Phenanthrenequinone was added to 10 ml of dioxane and 10 ml of 2M KOH (aq) in a stirred autoclave. After sealing and flushing with argon, the autoclave was heated to 150° C. for 5 hours. Fluorenone was the major product along with much smaller quantities of biphenyl. Carbon dioxide was detected in the gaseous product.

Example 24

Example 22 was repeated, but dioxane was replaced with toluene and the temperature raised to 200° C. The major product in the organic liquid layer was fluorenone and minor products were biphenyl and the 2-aldehyde of biphenyl. Both $CO_2$ and hydrogen were detected in the vapor phase.

What is claimed is:

1. A low severity process for upgrading hydrocarbonaceous feedstock containing polynuclear aromatic compounds, comprising the steps of:
   a. selectively oxidizing said feedstock under mild oxidation conditions in a multi-phase system, including at least one aqueous phase, using a water-soluble oxidation catalyst, said catalyst chosen to catalyze the selective oxygenation of non-terminal aromatic rings of polynuclear aromatic compounds in said feedstock;
   b. deoxygenating the product of said oxidation; and
   c. hydroprocessing the product of said deoxygenation to yield substantially mononuclear aromatic products.

2. The process as claimed in claim 1, wherein steps (a) and (b) of said process are practiced in the absence of hydrogen and said mild oxidation conditions comprise a temperature equal to or less than 275° C., and a pressure in the approximate range of 0 to 2000 psig.

3. The process as claimed in claim 2, wherein said temperature is in the approximate range of 100° C. to 180° C. and said pressure is in the approximate range of 100 to 200 psig.

4. The process as claimed in claim 3, wherein said temperature is in the approximate range of 120° C. to 180° C. and said pressure is in the approximate range of 300 to 500 psig.

5. The process as claimed in claim 1, wherein the non-terminal ring of said polynuclear aromatic compounds comprises the center ring of a three ring system.

6. The process as claimed in claim 1, wherein said oxidation catalyst is further selective to the oxidation of aromatic rings of said polynuclear aromatic compounds over non-aromatic functionalities of said compounds.

7. The process as claimed in claim 6, wherein said non-aromatic functionalities comprise alkyl or other side chains of said polynuclear aromatic compounds.

8. The process as claimed in claims 1 or 6, wherein at least a portion of said catalyst comprises water-soluble complexes of a transition metal or metals.

9. The process as claimed in claim 8, wherein said transition metals comprise a Group VIII metal or metals.

10. The process as claimed in claim 9, wherein at least one of said Group VIII metals comprises osmium.

11. The process as claimed in claim 8, wherein said catalyst further comprises a oxidation co-catalyst comprising water-soluble compounds capable of catalyzing the reoxygenation of said transition metal complexes.

12. The process as claimed in claim 11, wherein said oxidation co-catalyst compounds contain metals selected from the group consisting of vanadium, copper, iron, and cobalt.

13. The process as claimed in claim 8, wherein said water-soluble catalysts contain ligand structures incorporating halogenated aromatic functionalities.

14. The process as claimed in claim 1, wherein one of said phases comprises a water-containing emulsion.

15. The process as claimed in claim 1, wherein said hydrocarbonaceous feedstock is selected from the group consisting of crude petroleum, atmospheric residuum, vacuum residuum, heavy oil, asphalt, and coal liquid or other product of a coal liquefaction process.

16. The process as claimed in claim 1, further comprising, after said selective oxidation step, the steps comprising:

separating said aqueous phase containing said water-soluble oxidation catalyst from any non-aqueous phase or phases; and recycling said catalyst-containing aqueous phase to said selective oxidation step.

17. The process as claimed in claim 1, wherein said deoxygenation step is performed in a substantially alkaline environment.

18. The process as claimed in claim 17, wherein said alkaline environment comprises approximately two moles base per liter of water in contact with any non-aqueous phase.

19. The process as claimed in claim 1, wherein said deoxygenation step is carried out using a deoxygenation catalyst which further catalyzes said deoxygenation.

20. The process as claimed in claim 19, wherein said deoxygenation catalyst comprises compounds containing a Group VIII metal or metals, a macrocyclic ligand and a phosphine ligand.

21. The process as claimed in claim 20, wherein said Group VIII metal is selected from the group consisting of ruthenium and rhodium.

22. The process as claimed in claim 21, wherein said ruthenium is in a +2 oxidation state.

23. The process as claimed in claim 22, wherein said rhodium is in a +1 oxidation state.

24. The process as claimed in claim 1, wherein said hydroprocessing step is carried out in the absence of additional catalyst.

25. The process as claimed in claim 1, wherein said hydroprocessing step is carried out under mild hydroprocessing conditions.

26. The process as claimed in claim 25, wherein said mild hydroprocessing step comprises the substeps of:

charging the product of said deoxygenation step (b) and hydrogen into a reaction zone at a temperature above about 1000° F., a pressure in excess of about 100 psig, for a residence time of about 5 to 50 seconds, and at a hydrogen to hydrocarbon mole ratio between about 2:1 to 30:1 at the reactor inlet; and, separating desirable reaction products from unconverted material and hydrogen.

27. The process as claimed in claim 26, wherein said temperature range in said reaction zone is between about 1200° to 1400° F., said pressure range is between 300 to 800 psig, said residence time is between about 10 to 30 seconds, and said hydrogen to hydrocarbon mole ratio is between about 5:1 and 20:1.

* * * * *